United States Patent [19]

Kagara et al.

[11] Patent Number: 5,254,733
[45] Date of Patent: Oct. 19, 1993

[54] PROCESS FOR PRODUCING AN ALIPHATIC AMIDE AND SALTS THEREOF

[75] Inventors: Kooji Kagara, Minoo; Nobutaka Kawai, Osaka; Koji Machiya, Kobe; Kiyoaki Takasuka, Ikeda, all of Japan

[73] Assignee: Fujisawa Pharmaceutical Co., Ltd., Osaka, Japan

[21] Appl. No.: 775,456

[22] Filed: Oct. 15, 1991

[30] Foreign Application Priority Data

Oct. 31, 1990 [JP] Japan .................. 2-296815

[51] Int. Cl.$^5$ .................................... C07C 233/09
[52] U.S. Cl. .................................... 564/198
[58] Field of Search ............ 564/198, 197, 205, 206, 564/193

[56] References Cited

U.S. PATENT DOCUMENTS

| | | | |
|---|---|---|---|
| 4,456,603 | 6/1984 | Yamatsu et al. | 514/237.5 |
| 4,767,768 | 8/1988 | Okamoto et al. | 514/315 |
| 4,782,088 | 11/1988 | Okamoto et al. | 564/253 |

*Primary Examiner*—Allen J. Robinson
*Assistant Examiner*—Shailendra Kumar
*Attorney, Agent, or Firm*—Oblon, Spivak, McClelland, Maier & Neustadt

[57] ABSTRACT

The present invention relates to a process for producing (±)-(E)-4-ethyl-2-[E-hydroxyimino]-5-nitro-3-hexenamide.

6 Claims, No Drawings

PROCESS FOR PRODUCING AN ALIPHATIC AMIDE AND SALTS THEREOF

This invention relates to a process by which an aliphatic amide of the following general formula [I] or a salt thereof can be produced in a reduced number of steps and in good yield.

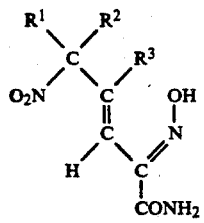
[I]

wherein $R^1$ through $R^3$ are the same or different and each means a hydrogen atom or a lower alkyl group.

Aliphatic amides of the above general formula [I] and salts thereof are known from Japanese Kokai Patent Application No. 59-152366 which discloses further that such compounds have vasodilating, antithrombotic and antianginal and other pharmacologic actions.

The process for production of the above compounds as described in the above laid-open patent literature comprises, for example, (1) reacting an aliphatic aldehyde as a starting material with an alkyl phosphonoacetate or the like to give the corresponding ester, (2) hydrolyzing the ester to give the free acid, (3) converting it to the amide, and (4) reacting the amide with dinitrogen trioxide or, in the presence of an acid, a nitrite.

However, the above process involves many steps and is therefore time-consuming and its very low overall yield makes the unit production cost high.

The object of this invention, accomplished under the above circumstances, is to provide a production process by which an aliphatic amide of the above formula [I] or a salt thereof can be produced in a reduced number of steps and in good yield.

This invention is directed to a process for producing an aliphatic amide of general formula [I] which comprises reacting an aliphatic aldehyde of general formula [II]:

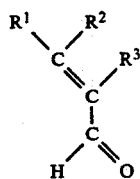
[II]

wherein $R^1$ through $R^3$ have the same meaning as defined hereinbefore, with a carbamoyl-containing Wittig reagent and reacting the reaction product, either without isolation or after isolation from the reaction mixture, further with dinitrogen trioxide or, in the presence of an acid, a nitrite.

The process according to this invention can be written as follows:

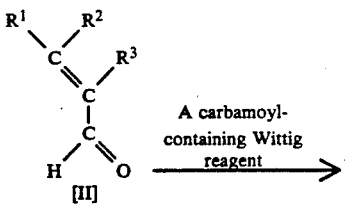

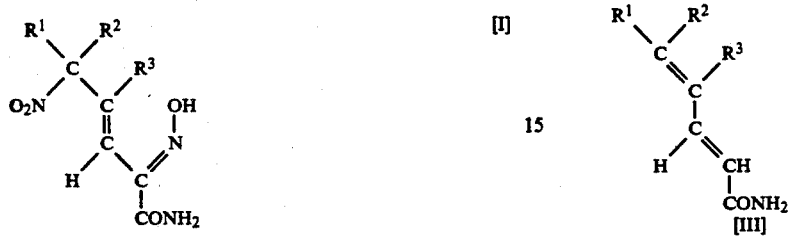

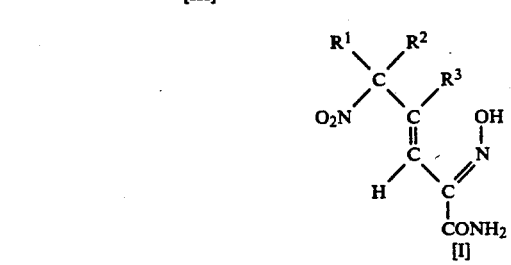

wherein $R^1$ through $R^3$ are as defined hereinbefore.

The various definitions applicable to the preferred working conditions of this invention are now described in detail.

As used in this specification, the term "lower alkyl group" means an alkyl group containing 1 to 6 carbon atoms, such as methyl, ethyl, propyl, butyl, pentyl, isopropyl, isobutyl and tert-butyl to name some preferred species.

The salts of compounds are pharmaceutically acceptable salts. Thus may be mentioned the corresponding salts with inorganic bases or organic bases, such as the salts with alkali metals, e.g. sodium, potassium, etc., salts with alkaline earth metals, e.g. calcium etc., the ammonium salts, and the salts with organic amines, e.g. ethanolamine, triethylamine, dicyclohexylamine and so on.

The carbamoyl-containing Wittig reagent to be employed in this invention includes, inter alia, Wittig reagents of the following general formula:

$$Y—CONH_2 \quad [IV]$$

wherein Y means a group represented by

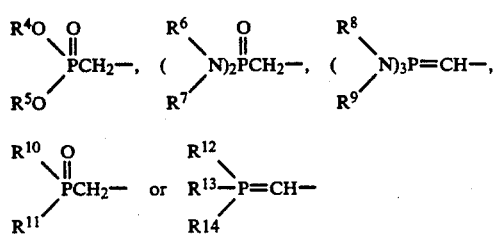

wherein $R^4$ through $R^9$ are the same or different and each means a lower alkyl group; $R^{10}$–$R^{14}$ are the same or different and each means a phenyl group or a lower alkyl-substituted phenyl group. The following is a partial listing of specific examples.

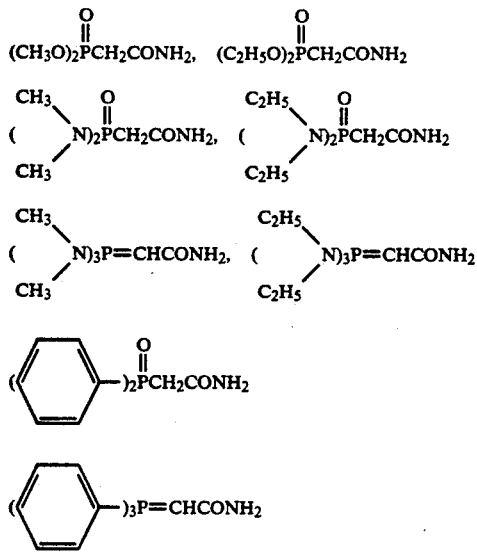

The carbamoyl-containing Wittig reagent can be easily made available, for example by reacting a lower alkoxycarbonyl-containing Wittig reagent with ammonia.

In reducing this invention to practice, an aliphatic aldehyde of the general formula [II] presented hereinbefore is dissolved in an appropriate solvent and, preferably with stirring in a nitrogen gas atmosphere, said Wittig reagent is added for reaction. The solvent may be chosen from among a variety of species which do not interfere with the reaction, such as dichloromethane, dioxane and tetrahydrofuran or a mixture thereof. This reaction may be conducted under cooling, at room temperature or under moderate heating, although it is preferably carried out in the neighborhood of 0° C. While the reaction time is dependent on the reaction temperature, among other conditions, it is generally sufficient to continue the reaction for about 1 to 10 hours.

This reaction is preferably carried out in the presence of a base.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, sodium bicarbonate, calcium hydroxide, etc.), ammonium hydroxide; an organic base such as an alkoxide or phenoxide of the above metal [e.g. sodium ethoxide, sodium methoxide, potassium tert-butoxide, etc.), an amine such as mono-, di or tri- alkylamine (e.g. methylamine, ethylamine, N,N-dimethyl-1,3-propanediamine, trimethylamine, triethylamine, etc.).

The above reaction gives rise to an intermediate compound of the general formula [III] presented hereinabove and this reaction product, either without isolation or after isolation, can be further reacted with dinitrogen trioxide, to give the desired compound of general formula [I]. Since dinitrogen trioxide is generally prepared by reacting a nitrite with an acid, said intermediate product may be reacted with a nitrite in the presence of an acid to produce the desired compound. The preferred examples of the nitrite are the alkali metal salts such as the sodium salt, potassium salt, etc. and the alkaline earth metal salts such as the calcium salt. The acid may be an inorganic acid or an organic acid, preferably being hydrochloric acid, sulfuric acid, formic acid or acetic acid. This reaction can also be conducted in the presence of a solvent similar to that mentioned hereinbefore, either at ordinary temperature, under cooling or under moderate heating. The reaction time may be about 1 to 10 hours.

Although the intermediate compound may be isolated as mentioned above, it is more advantageous, in terms of processability and yield, to conduct the subsequent reaction without isolating the intermediate product.

The crude product compound thus obtained can be purified in the routine manner, for example by recrystallization, to give the desired compound of high purity grade in good yield.

The object compound [I] and the intermediate compound [III] include one or more isomers due to the asymmetric carbon atoms and all of such isomers are included within the scope of this invention.

According to this invention, the pharmacological active substance of the general formula [I] can be produced in a reduced number of steps and with remarkably enhanced yield and productivity. Especially, among the compounds of the general formula [I], (±)-(E)-4-ethyl-2-[(E)-hydroxyimino]-5-nitro-3-hexenamide has an excellent pharmacological activity and about this compound clinical studies are now under way. Accordingly, it is very valuable industrially to produce this compound in a reduced number of steps and with remarkably enhanced yield and productivity.

According to the process of this invention, a total yield of (±)-(E)-4-ethyl-2-[(E)-hydroxyimino]-5-nitro-3-hexenamide is remarkably enhanced as compared with the prior art process as mentioned before. That is, as an example, a total yield of this compound prepared from 2-ethylcrotonaldehyde according to the process of this invention was 71% and that by the prior art process was 32%.

The following Example is given for the purpose of illustrating this invention.

EXAMPLE

Preparation of a carbamoyl-containing Wittig reagent

In 400 ml of 25% aqueous ammonia is dissolved 100 g (0.446 mol) of ethyl diethylphosphonoacetate at an temperature of not higher than 10° C. The solution is allowed to stand overnight at an temperature of not higher than 15° C. and concentrated under reduced pressure. To the residue is added 25 ml of toluene and the water is azeotropically removed off under reduced pressure. To the residue is added 300 ml of toluene and 100 ml is azeotropically removed off under atmospheric pressure for complete dehydration. The residual solution is cooled and seed crystals are added at 50° C. for crystallization. After cooling to 5° C., the crystals are collected by filtration. The crystals are washed with 100 ml of toluene and dried in vacuo overnight to give 76.7 g of diethylphosphono-acetamide (a carbamoyl-containing Wittig reagent) (Yield 88.0%).

IR (Nujol):3350, 3180, 1660, 1240 cm$^{-1}$ $^1$H NMR (DMSO-d$_6$, δ):1.23 (6H, tr, J=7 Hz), 2.89 (2H, d, J=11 Hz), 4.01 (4H, m), 7.05 (1H, bs), 7.39 (1H, bs)

Production of (±)-(E)-4-ethyl-2-[(E)-hydroxyimino]-5-nitro-3-hexenamide (an object compound)

In 500 ml of methylene chloride is dissolved 218.7 g (1.12 mols) of the diethylphosphonoacetamide prepared above in a nitrogen atmosphere with stirring. The solution is cooled and 125.8 g (1.12 mols) of potassium tert-butoxide is added at $-10°\sim 0°$ C., followed by dropwise addition of 100 g (1.02 mols) of 2-ethylcrotonaldehyde at the same temperature. After completion of dropwise addition, the reaction is continued at the same temperature for 2 hours. The reaction mixture is then dissolved by addition of 250 ml of water and 225.0 g (3.26 mols) of sodium nitrite and 500 ml of 17.5% hydrochloric acid is then added dropwise at $-10°\sim 0°$ C. over $1\sim 1.5$ hours. After completion of dropwise addition, the reaction is continued at the same temperature for 1 hour. The reaction mixture is then allowed to stand at the same temperature for 30 minutes and the crystals are collected by filtration. The crystals are then washed serially with 1 l of cold water, 1 l of cold methylene chloride, 500 ml of cold water and 500 ml of cold methylene chloride and dried in vacuo overnight to give 179.8 g of (±)-(E)-4-ethyl-2-[(E)-hydroxyimino]-5-nitro-3-hexenamide as crude crystals (Yield 82%).

The above crystals are dissolved in 2.1 l of 65% aqueous solution of isopropyl alcohol, treated with charcoal and cooled to 5° C., and diluted with water. The crystals are collected by filtration, washed with 360 ml of 25% aqueous solution of isopropyl alcohol and dried in vacuo overnight to give 156.4 g of (±)-(E)-4-ethyl-2-[(E)-hydroxyimino]-5-nitro-3-hexenamide as pure crystals (Yield 87.0%).

IR (Nujol):3460, 3200, 1660, 1550, 1000 cm.$^{-1}$ $^1$H NMR (DMSO-d$_6$, δ):0.92 (3H, tr, J=8 Hz), 1.60 (3H, d, J=7 Hz), 2.06 (2H, q, J=7 Hz), 5.41 (1H, q, J=7 Hz), 6.16 (1H, s), 7.31 (1H, s), 7.47 (1H, s), 11.9 (1H, s)

Preparation of (±)-(E)-4-ethyl-2-[(E)-hydroxyimino]-5-nitro-3-hexenamide by a prior art method

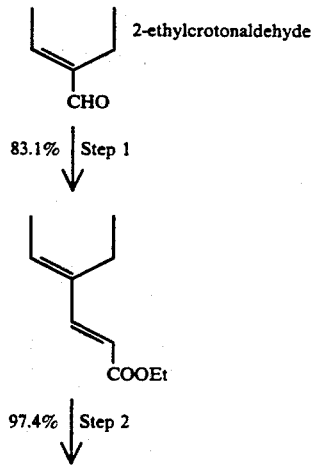

Preparation of (±)-(E)-4-ethyl-2-[(E)-hydroxyimino]-5-nitro-3-hexenamide by a prior art method -continued

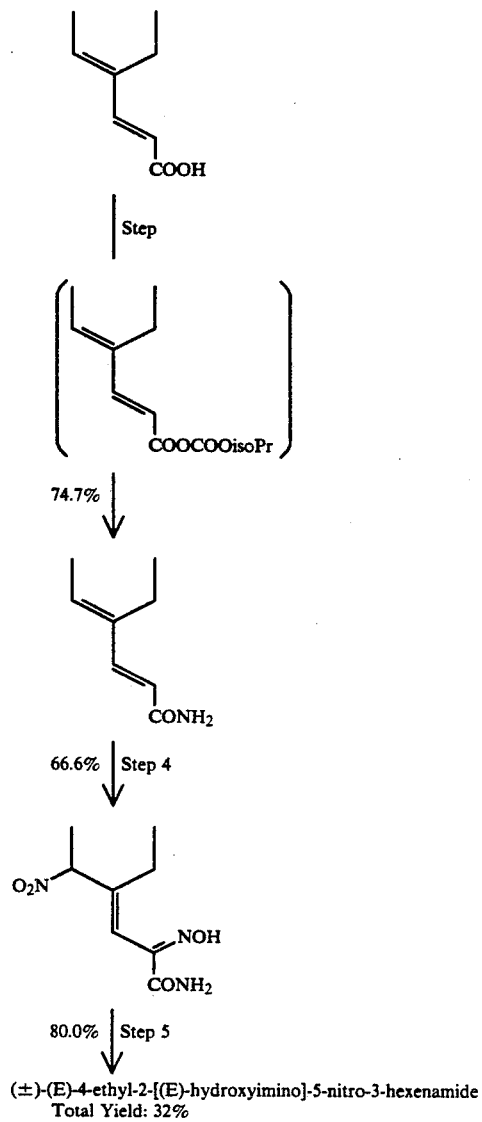

(±)-(E)-4-ethyl-2-[(E)-hydroxyimino]-5-nitro-3-hexenamide
Total Yield: 32%

Step 1

To a solution of 12.7 kg (235 mol) of sodium methoxide and 48.0 kg (214 mol) of ethyl diethylphosphonoacetate in 40 l of methanol is added dropwise 20 kg (204 mol) of 2-ethylcrotonaldehyde at 20°-30° C. during 0.5 hour. After stirring for 2 hours at same temperature, the reaction mixture is poured into the solution of 180 l of water and 120 l of toluene. The toluene layer is separated and combined with 50 l toluene extract of aqueous phase, and washed with two 120 l portions of saturated sodium chloride solution. After drying over anhydrous magnesium sulfate, the solvent is removed and the residue is distilled under reduced pressure to give ethyl (E,E)-4-ethyl-2,4-hexadienoate (Yield 28.5 kg) (83.1%), b.p. 41°-75° C./5-8 mmHg.

Step 2

To a solution of 20.0 kg (119 mol) of ethyl (E,E)-4-ethyl-2,4-hexadienoate in 15 l of methanol is added a solution of 6.0 kg (150 mol) of sodium hydroxide in 60

1 of water. The mixture is heated at 50°-55° C. for 1 hour and then cooled to 20°~25° C., poured into a 8%-hydrochloric acid solution at same temperature. The precipitate formed is collected by filtration, washed with 200 l of water and dried in vacuo overnight to give 16.2 kg of (E,E)-4-ethyl-2,4-hexadienoic acid (Yield 97.4%).

Step 3

To a solution of 16.0 kg (114 mol) of (E,E)-4-ethyl-2,4-hexadienoic acid and 11.5 kg (114 mol) of triethylamine in 112 l of dichloromethane is added dropwise 14.0 kg (114 mol) of isopropyl chloroformate at −5°~−10° C. and the reaction is continued for 1 hour at same temperature. To this solution is introduced 7.4 kg (435 mol) of anhydrous ammonia gas and allowed to stand overnight at 20°-30° C. The solvent and excess ammonia gas is removed under reduced pressure. The residue is dissolved in 128 l of ethyl acetate and washed with 80 l of 5%-sodium chloride solution, 80 l of 5%-hydrochloric acid solution, 80 l of 5%-sodium chloride solution, 80l of 7%-sodium hydroxide solution and 80 l of 5%-sodium chloride solution respectively. The solvent is removed under reduced pressure to give 11.9 kg of (E,E)-4-ethyl-2,4-hexadienamide as a yellow oil (Yield 74.7%).

Step 4

To a solution of 10.0 kg (71.8 mol) of (E,E)-4-ethyl-2,4-hexadienamide and 19.8 kg (287 mol) of sodium nitrite in 100 l of dioxane and 70 l of water is added dropwise 13 l of 35% hydrochloric acid at 15°-20° C. during 2 hours under vigorous stirring. The reaction is continued for 0.5 hour after the addition is completed. The precipitate formed is collected by filtration, washed with 20 l of cold water. The cakes are suspended in 100 l of cold water for 0.5 hour, then filtered, washed with 20 l of cold water. The cakes are suspended again in 50 l of dichloromethane at 20°-25° C. for 0.5 hour, then filtered, washed with 80 l of dichloromethane and dried in vacuo overnight to give 10.3 kg of crude (±)-(E)-4-ethyl-2-[(E)-hydroxyimino]-5-nitro-3-hexenamide (Yield 66.6%).

Step 5

To a solution of 10.0 kg (46.5 mol) of crude (±)-(E)-4-ethyl-2-[(E)-hydroxyimino]-5-nitro-3-hexenamide in 140 l of ethanol is added dropwise 20 l of water at 20°-25° C. during 15 minutes. After stirring for 30 minutes, 1.0 kg of charcoal is added and filtered. Filtrate is cooled to 10°-15° C. and diluted with 260 l of water. After cooling to 0°-5° C., the crystals formed are collected by filtration, washed with 20 l of 25%-aqueous ethanol solution and dried in vacuo overnight to give 8.0 kg of pure (±)-(E)-4-ethyl-2-[(E)-hydroxyimino]-5-nitro-3-hexenamide (Yield 80%).

We claim:

1. A process for producing (±)-(E)-4-ethyl-2-[(E)-hydroxyimino]-5-nitro-3-hexenamide, comprising reacting 2-ethylcrotonaldehyde, with a carbamoyl-containing Wittig reagent and reacting the reaction product, either without isolation or after isolation, further with a dinitrogen trioxide or, in the presence of an acid, and a nitrite.

2. A process according to claim 1 wherein said carbamoyl-containing Wittig reagent has the general formula:

$$Y-CONH_2 \qquad [IV]$$

wherein Y is a group represented by

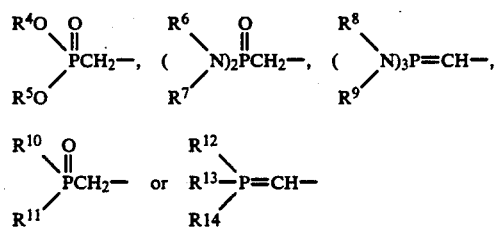

wherein $R^4$ through $R^9$ are the same or different and each means a lower alkyl group; $R^{10}$ through $R^{14}$ are the same or different and each means a phenyl group or a lower alkyl-substituted phenyl group.

3. A process according to claim 1, wherein said carbamoyl-containing Wittig reagent has the general formula:

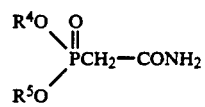

wherein $R^4$ and $R^5$ are each a lower alkyl group.

4. The process of claim 1 wherein said carbamoyl-containing Wittig reagent is diethylphosphonoacetamide.

5. A process according to claim 4, wherein the reaction is conducted in the presence of a base.

6. A process according to claim 5, wherein the base is potassium tert-butoxide.

* * * * *